(12) United States Patent
Mawson (10) Patent No.: US 8,883,512 B1
(45) Date of Patent: Nov. 11, 2014

(54) METHOD FOR DIAGNOSING GESTATIONAL DIABETES, PREECLAMPSIA, AND FETAL GROWTH RESTRICTION

(76) Inventor: Anthony R. Mawson, Jackson, MS (US)

( * ) Notice: Subject to any disclaimer, the term of this patent is extended or adjusted under 35 U.S.C. 154(b) by 0 days.

(21) Appl. No.: 13/430,511

(22) Filed: Mar. 26, 2012

Related U.S. Application Data (60) Provisional application No. 61/467,770, filed on Mar. 25, 2011.

(51) Int. Cl.
*G01N 33/52* (2006.01)
*G01N 33/82* (2006.01)
*A61N 1/32* (2006.01)

(52) U.S. Cl.
USPC ............................. 436/129; 436/128; 436/127

(58) Field of Classification Search
CPC ..... G01N 33/52; G01N 33/82; G01N 31/714; A61N 1/326; A61N 1/328; A61N 1/205; A61N 1/32; A61N 1/40
USPC ..................... 436/129, 128, 127; 607/50, 2, 1
See application file for complete search history.

(56) References Cited

U.S. PATENT DOCUMENTS

| | | | |
|---|---|---|---|
| 2005/0148023 A1* | 7/2005 | Thadhani et al. | 435/7.1 |
| 2009/0280124 A1* | 11/2009 | Labat et al. | 424/139.1 |
| 2010/0113610 A1* | 5/2010 | Kim et al. | 514/725 |

OTHER PUBLICATIONS

Penniston Kristina L., The acute and chronic toxic effects of vitamin A, Am J Clin Nutr, 2006, 83, 191-201.*

* cited by examiner

*Primary Examiner* — Christine T Mui
(74) *Attorney, Agent, or Firm* — Joseph S. Bird, III; Bradley Arant Bould Cummings LLP (57) ABSTRACT

A serum-based biomarker for diagnosing gestational diabetes, preeclampsia and fetal growth restriction (GDM-PREEC-FGR), based on retinoid profiling, and a method for diagnosing GDM-PREEC-FGR that specifically uses a blood sample to identify and measure the concentrations of retinol (vitamin A alcohol), retinyl esters and retinoic acid.

8 Claims, 5 Drawing Sheets

METHOD FOR DIAGNOSING GESTATIONAL DIABETES, PREECLAMPSIA, AND FETAL GROWTH RESTRICTION

PRIORITY CLAIM

This application claims priority to U.S. nonprovisional application No. 61/467,770 filed on Mar. 25, 2011.

FIELD OF THE INVENTION

The field of this invention is the diagnosis and treatment of gestational diabetes, preeclampsia, and fetal growth restriction (GDM-PREEC-FGR). The first aspect of this invention is a new biomarker for diagnosing GDM-PREEC-FGR, based on serum retinoid (vitamin A) profiling using, e.g., the method of high performance liquid chromatography (HPLC). The invention enhances the early identification of these conditions and provides new avenues for treatment to prevent their long-term sequelae, i.e., later-onset metabolic syndrome and atherosclerotic heart disease. The new method uses serum retinoid profiling as a basis for diagnosing GDM-PREEC-FGR, whereby the concentrations, ratios and percentage values of these compounds are used, individually and in concert, to make the diagnosis. Employing the biomarker to diagnose GDM-PREEC-FGR entails obtaining venous blood in sufficient quantity (about 5 mL) from a woman early in pregnancy; analyzing the blood (about 5 mL) for retinoids (vitamin A and its congeners) using, e.g., HPLC or other validated analytic methods, and determining the concentrations of retinol (vitamin A alcohol), retinyl esters (the storage form of vitamin A), and retinoic acid (RA) (the major biological active metabolite of vitamin A). The diagnosis of GDM-PREEC-FGR will be suspected when the percent of retinyl esters to total vitamin A (retinyl esters plus retinol) exceeds 10%. The second aspect of this invention is a new treatment for GDM-PREEC-FGR, using a retinoid receptor antagonist.

BACKGROUND TO THE INVENTION AND PRIOR ART

Gestational diabetes occurs in about 4% of pregnancies in the U.S. (Getahun, 2008), increasing with maternal age and body mass index (Engelgau et al., 1995). GDM is associated with increased risks of perinatal mortality and congenital malformations (Sepe et al., 1985), pregnancy-induced hypertension and FGR, but the causes are not well understood (American Pregnancy Association, 2004). Children of women with GDM are also at increased risk for obesity and abnormal glucose tolerance by the time of puberty (Schneider and Rayfield, 2002). Preeclampsia, the most common hypertensive disorder of pregnancy, defined by the triad of hypertension, proteinuria and edema, occurs in 6-10% of pregnancies and is the leading cause of maternal mortality in Western countries (Great Britain Department of Health, Why Mothers Die: Report on Confidential Enquiries into maternal Deaths in the United Kingdom 1994-1996. London, TSO, 1998). A characteristic feature of the disorder is that it usually resolves after delivery of the fetus and placenta. Progressive fetal growth restriction associated with preeclampisa is a leading cause of perinatal morbidity and mortality (National High Blood Pressure Education Program Working Group Report on High Blood Pressure in Pregnancy. *Am J Obstet Gynecol* 1990; 163:1691-1712). Current treatment options are limited and include bed rest, magnesium sulfate administration to prevent convulsions, and early delivery. The cause of preeclampsia remains uncertain but a primary role is attributed to the placenta and to poor placental perfusion resulting in hypoxia and increased oxidative stress.

Preeclampsia is commonly associated with fetal growth restriction (FGR), small-for-gestational-age (SGA) birth, and preterm delivery (Sibai et al., 2005) as well as gestational diabetes (Carpenter, 2007). The maternal syndrome of preeclampsia and its fetal counterpart, fetal growth restriction (FGR), present a continuing conundrum: while these conditions are associated with each other and with other de novo or preexisting metabolic abnormalities, the precise sequence of events and the causal mechanisms underlying these conditions and their long-term sequelae are uncertain. A predominant view is that preeclampsia is initiated by inadequate trophoblast invasion of the arterioles by the cytotrophoblast, which leads to incomplete remodeling of the uterine spiral arteries and to a state of placental hypoxia (Roberts et al., 1989; Conrad and Benyo, 1997; Gilbert et al., 2008). The poorly perfused placenta in turn synthesizes and releases vasoactive factors, including soluble VEGF receptor 1 (sVEGFR1, also known as soluble fms-like tyrosine kinase-1 or sFlt-1), soluble endoglin (sEng), angiotensin II type-1 receptor autoantibodies, and cytokines such as tumor necrosis factor-alpha, which generate widespread dysfunction of the maternal vascular endothelium, resulting in hypertension and other features of preeclampsia. Endothelium-derived relaxing and contracting factors maintain vascular homeostasis, and the ischemic placenta is believed to induce endothelial dysfunction in the maternal vasculature by altering the balance between angiogenic and antiangiogenic factors, in particular sFlt-1, in favor of the latter (Maynard et al., 2003, Karumanchi et al., 2005). Angiogenic factors include vascular endothelial growth factor (VEGF) and placental growth factor (PlGF). sFlt-1 appears early in the circulation, before the clinical onset of preeclampsia (Levine et al., 2006). Although the precise sequence of events in the placental release of sFlt-1 is uncertain (Karumanchi et al., 2004), the initiating event in preeclampsia is assumed to be reduced uteroplacental perfusion as a result of abnormal cytotrophoblast invasion of the spiral arterioles. The fact that preeclamptic symptoms develop during pregnancy and generally cease after delivery is taken as evidence that the placenta is the primary cause of the condition.

A well-characterized experimental model of preeclampsia involves clamping the uterine artery to produce a hypoxic condition in the placenta (the Reduced Uterine Perfusion Pressure, or RUPP model). RUPP-induced hypertension in the rat is associated with marked cardiovascular dysfunction similar to that seen in women with preeclampsia (Schlook et al., 2007) as well as an imbalance of angiogenic factors, including increased sFlt-1 and decreased VEGF and PlGF (Gilbert et al., 2007). Clinical evidence also indicates an imbalance between proangiogenic VEGF and PlGF, and antiangiogenic sFlt-1 in preeclampsia (Lam et al., 2005). Thus a working hypothesis is that the maladaptive overexpression of soluble VEGF receptor 1 (sVEGFR1) and its antagonism of VEGF bioactivity contribute to the deficient angiogenic response that results in PREEC-FGR. Plasma and amniotic fluid concentrations of sFlt-1 are increased in patients with preeclampsia and in placental sFlt-1 mRNA (Maynard et al., 2003). Increases in sFlt-1 and sEng predict preeclampsia, since concentrations rise before manifestations of overt symptoms of hypertension and proteinuria (Lam et al., 2005; Levine et al., 2006). Conversely, VEGF infusion attenuates the increased blood pressure and renal damage seen in pregnant rats overexpressing sFlt-1 (Li et al., 2007). In the pregnant rat, uteroplacental ischemia increases placental sFlt-1 and is associated with decreased VEGF and PlGF in late gestation; adenovirus-mediated combined increases in sFlt-1 and sEng also exacerbate the effects of either factor alone, resulting in fetal growth restriction as well as severe hypertension and proteinuria (Venkatesha et al., 2007). Markers of endothelial dysfunction, in particular nitric oxide (NO), are also associated with preeclampsia. Chronic NO synthase inhibition in pregnant rats leads to hypertension and associated peripheral and renal vasoconstriction, proteinuria, FGR, and increased fetal death (Gilbert et al., 2008).

In summary, considerable evidence supports the hypothesis of reduced placental perfusion as a cause of preeclampsia and FGR; similarly, the link between FGR, preeclampsia and later-onset vascular disease is thought to result from an initial state of reduced utero-placental perfusion (Granger et al., 2001). High rates of low birth weight (LBW) in the United States and other western countries are also attributed to defective uteroplacental perfusion rather than maternal malnutrition (Henriksen et al., 1997). In rats, placental insufficiency/ischemia induced by uterine artery ligation in mid- to late-gestation results in LBW offspring that are predisposed to develop hypertension (Alexander, 2003).

There are several limitations to this theory. First, the stimulus that initiates the failure of cytotrophoblasts to invade the spiral arterioles and the resulting reduction in placental perfusion is unknown. Second, maternal factors unrelated to the placenta also contribute to the risk of preeclampsia and SGA birth. For instance, preeclampsia is associated with the metabolic syndrome that includes chronic hypertension (Samadi et al., 2001), elevated serum triglycerides and free fatty acids, insulin resistance and glucose intolerance. Insulin resistance can also precede preeclampsia and is associated with the overall syndrome of preeclampsia. Triglyceride-rich lipoproteins associated with low-density lipoproteins are significantly increased in women who develop preeclampsia. Obesity is also strongly associated with preeclampsia and increased plasma triglyceride concentration, and can be associated with SGA, LGA, and preterm birth (Rajasingam et al., 2009). To determine whether metabolic derangements follow or precede placental ischemia, a study using the RUPP model found that metabolic syndrome-like derangements are not a direct consequence of RUPP but contribute to cardiovascular dysfunction in preeclampsia independently of poor placental perfusion. Third, other known correlates of preeclampsia are not satisfactorily explained on the hypothesis of poor placental perfusion including, e.g., the association of preeclampsia with neutrophils and neutrophilic activation (Cadden and Walsh, 2008; Tsukimori et al., 2008); low serum vitamin A (Ziari et al., 1996; Zhang et al., 2001; Wardle et al., 2001); hyperuricemia, which develops as early as 10 weeks of gestation in women who later develop preeclampsia (Koopmans et al., 2008; Bainbridge et al., 2009); headache (Contag et al., 2009; Facchinetti et al., 2009); and the long-term increased risk of cardiovascular disease (Craici et al., 2008). These observations call for new insights into the causes of preeclampsia, FGR/SGA birth and subsequent increased risks of vascular disease.

SUMMARY OF THE INVENTION

The invention described herein is a new serum biomarker (i.e., biochemical screening test) for detecting gestational diabetes, preeclampsia and fetal growth restriction (GDM-PREEC-FGR) via retinoid profiling; that is, by assessing the concentrations, ratios and percentages of retinol (vitamin A alcohol), retinyl esters (the storage form of vitamin A) and retinoic acid (the major biologically active metabolite of retinol) using, e.g., high performance liquid chromatography (HPLC) or other valid analytic methods. What is claimed is a new biochemical marker or screening tool for identifying GDM-PREEC-FGR based on retinoid profiling; more specifically, a profile comprising low or normal concentrations of retinol, a high (greater than 10%) percent retinyl esters as a fraction of total vitamin A (retinyl esters plus retinol), and increased retinoic acid concentrations. A second aspect of this invention, based on the retinoid toxicity hypothesis described herein, is the use of a retinoid receptor antagonist to treat GDM-PREEC-FGR.

A retinoid biomarker is claimed for diagnosing gestational diabetes (GDM), preeclampsia (PREEC) and fetal growth restriction (FGR), based on profiling of serum retinoids (vitamin A and its congeners) by the best known method of high performance liquid chromatography (HPLC). These conditions tend to co-exist in pregnancy. The pathogenesis of GDM-PREEC-FGR and the links between them are not well understood and there is no established biomarker for diagnosing the combined problem of GDM-PREEC-FGR, especially in early, asymptomatic phases. The existence of such a marker would greatly aid in the prevention and management of these conditions. A potentially important clue to understanding the pathogenesis of GDM-PREEC-FGR is the consistent finding of low serum retinol concentrations in preeclampsia and in low birth weight infants. Although these are often interpreted as indicating vitamin A deficiency, reduced serum retinol concentrations can indicate liver dysfunction and impaired hepatic mobilization of the vitamin. A signal from the conceptus may initiate mild cholestatic liver dysfunction, inducing an endogenous form of retinoid toxicity that contributes to gestational diabetes, preeclampsis and fetal growth restriction in women who are already susceptible due to preexisting conditions affecting the liver. Retinoids (vitamin A and its congeners) are essential for many biological functions but toxic in higher concentration, especially if major shifts occur in the tissue distribution of retinoids as a result of liver damage. Liver dysfunction not only entails impaired glucose uptake, leading to abnormal glucose metabolism (i.e., GDM), but also impairs the mobilization and secretion of vitamin A as retinol-binding protein (RBP), resulting in reduced serum retinol concentrations. At the same time, due to liver dysfunction, toxic concentrations of stored retinoids (e.g., retinyl esters, retinoic acid) are spilled into the circulation, inducing preeclampsia, fetal growth restriction and a spectrum of other adverse maternal and fetal effects, depending on the timing of exposure and the concentration of retinoids. Evidence for this hypothesis was obtained from an experiment using an animal model of gestational diabetes and preeclampsia, in which the presence of liver damage was indicated by elevated liver enzymes (Mawson A R et al. Altered retinoid profiles in an animal model of preeclampsia, gestational diabetes and fetal growth restriction. *Reproductive Science* 2010; 17 Suppl: Abstract 592). Retinoid profiles were significantly altered compared to those of control animals: retinol concentrations were significantly reduced (median, 0.45 vs. 1.04 µmol/L; p-value=0.012), but it was also found that percent retinyl esters as a fraction of total vitamin A >10%—an accepted indicator of retinoid toxicity—was significantly increased (median, 24% vs. 11%; p-value=0.008). The concentration of retinoic acid, the major biologically active metabolite of retinol, was also significantly increased (median, 0.0155 vs. 0.0075 µmol/L; p-value=0.045). Retinoid profiling provides a new biomarker for diagnosing GDM-PREEC-FGR as a basis for both established and new approaches to the prevention and treatment of these conditions and their long-term sequelae. The present invention is therefore a new biomarker for diagnosing GDM-PREEC-FGR that uses serum retinoid profiling for diagnosing these conditions in one embodiment, by the method of HPLC, in which the concentrations, ratios and percentage values of these compounds are used, individually and in concert, to make the diagnosis. In particular, percent retinyl esters as a fraction of total serum vitamin A (i.e., retinol plus retinyl esters) is a new diagnostic biomarker for GDM-PREEC-FGR. Evidence is also presented from a preliminary study in support of the claim to have invented a new treatment for GDM-PREEC-FGR using a retinoid receptor antagonist.

DETAILED DESCRIPTION

The author hypothesizes that GDM-PREEC-FGR collectively result from liver dysfunction and adverse effects resulting from the spillage of toxic concentrations of stored vitamin A compounds (retinoids) into the maternal and fetal circulation (the "retinoid toxicity hypothesis"). A review of the literature and preliminary evidence derived from an experiment by the author using an animal model of gestational diabetes and preeclampsia, in which liver damage was detected by elevated liver enzymes, has suggested a new screening tool for diagnosing GDM-PREEC-FGR that involves determining the serum concentrations of retinol, retinyl esters and retinoic acid; and in particular, determining the percent of retinyl esters as a fraction of total vitamin A (retinol plus retinyl esters). Although further research is needed to confirm the hypothesis, determining the percent of retinyl esters as a fraction of total vitamin A may provide a sensitive and specific biomarker for GDM-PREEC-FGR, and levels in excess of 10% (an accepted criterion of vitamin A toxicity) are expected to indicate the presence of GDM-PREEC-FGR.

Figure 1:
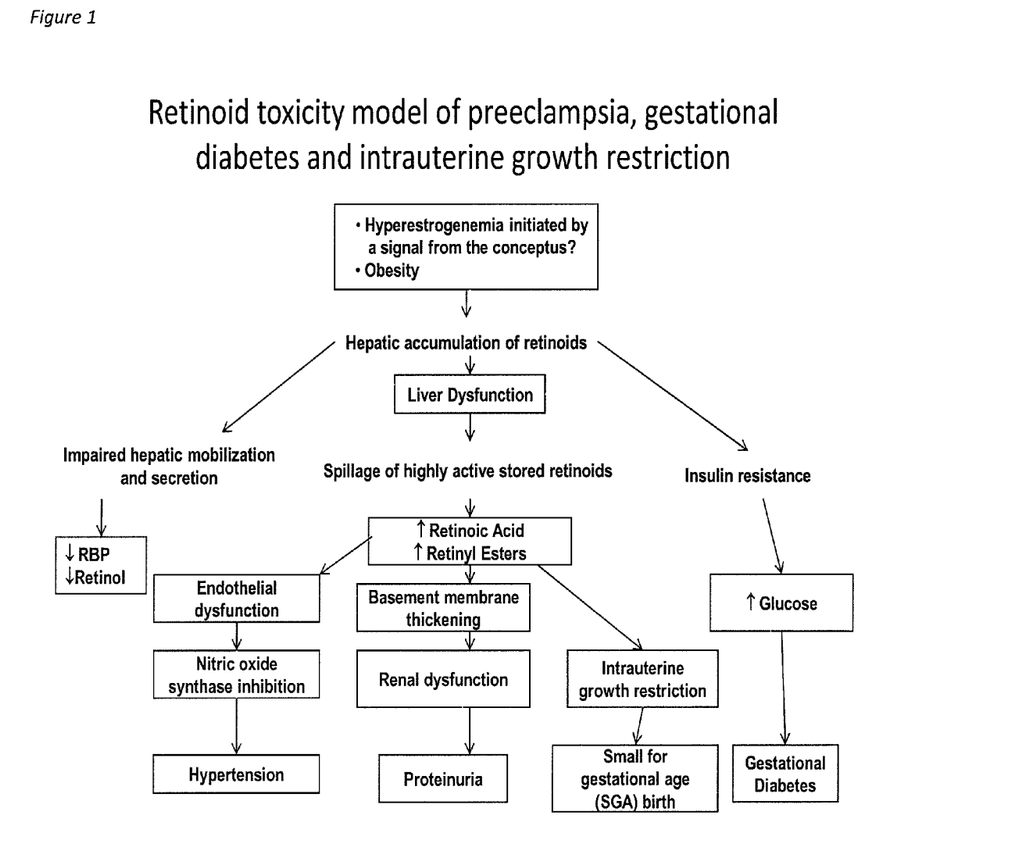
FIG. 1 shows a retinoid toxicity model of gestational diabetes (GDM), preeclampsia (PREEC) and fetal growth restriction (FGR).
Figure 2:
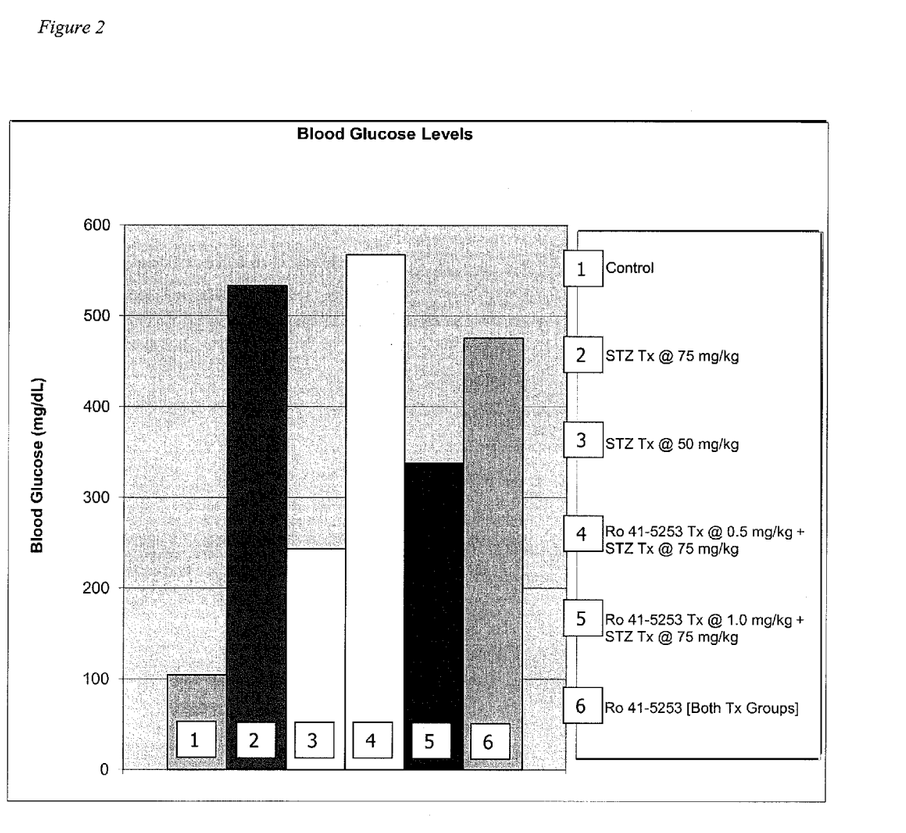
FIG. 2 is a graph showing that blood glucose levels were reduced by the higher dose of Ro41-5253 but not by the lower dose.
Figure 3:
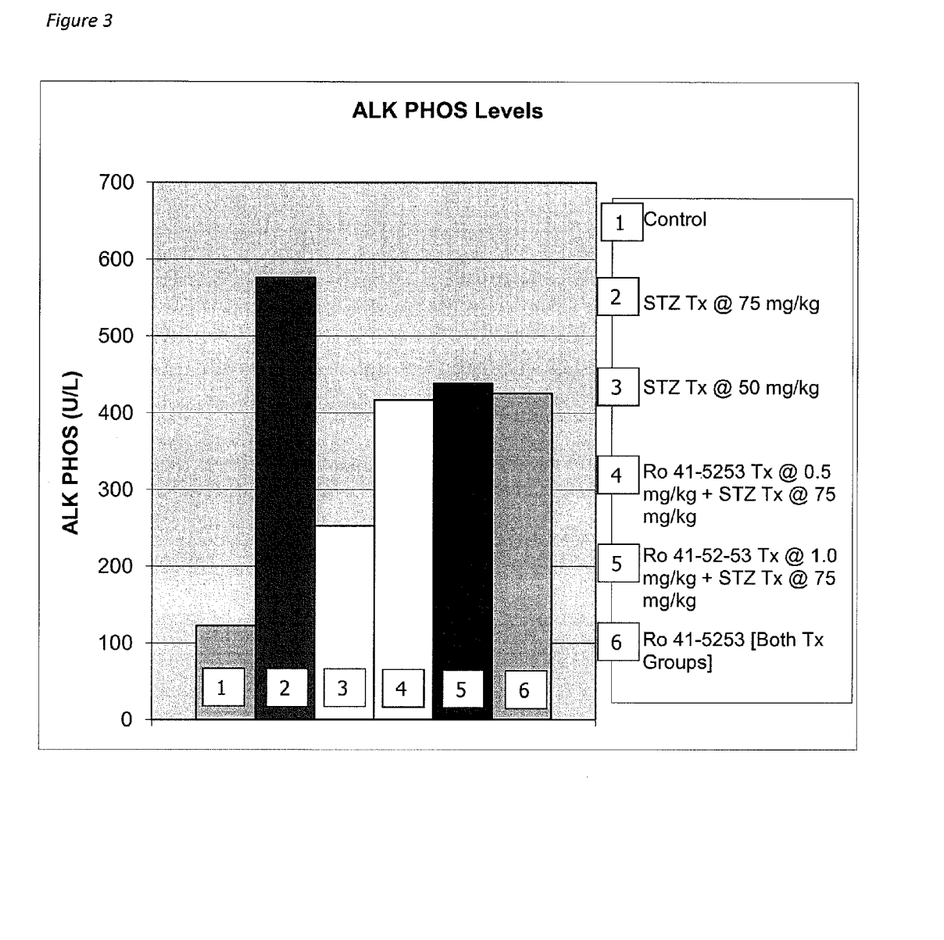
FIG. 3 is a graph showing that alkaline phosphatase levels induced by STZ at 75 mg/kg were slightly reduced (about 20%) by the retinoid receptor antagonist.
Figure 4:
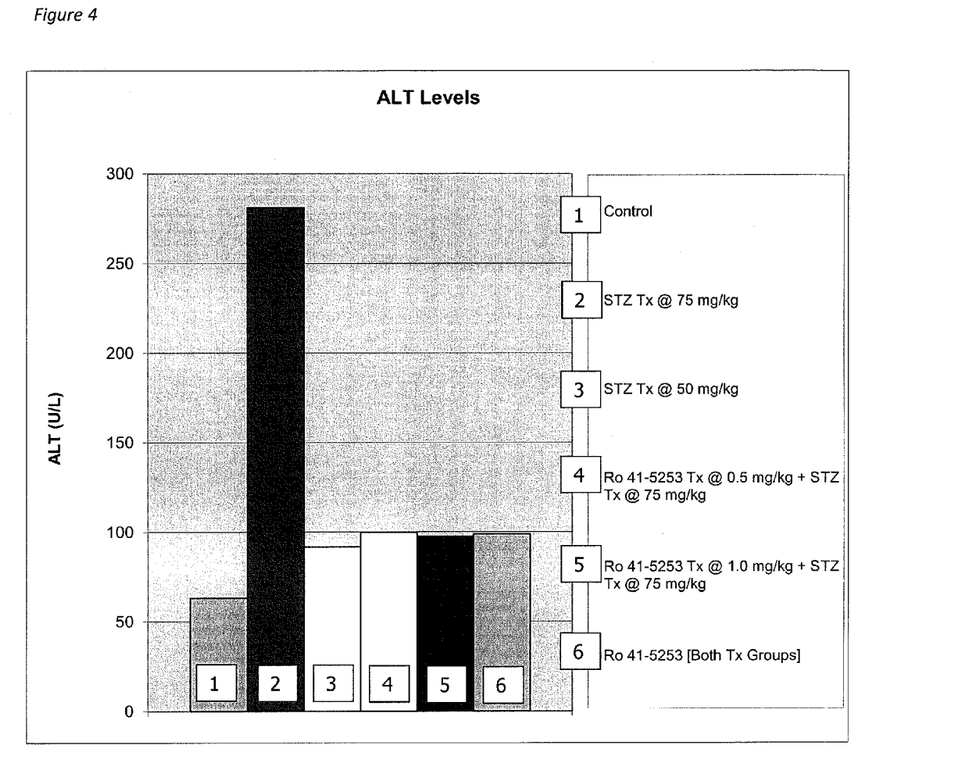
FIG. 4 is a graph showing that alanine aminotransferase levels induced by STZ at 75 mg/kg were markedly reduced by the retinoid receptor antagonist.
Figure 5:
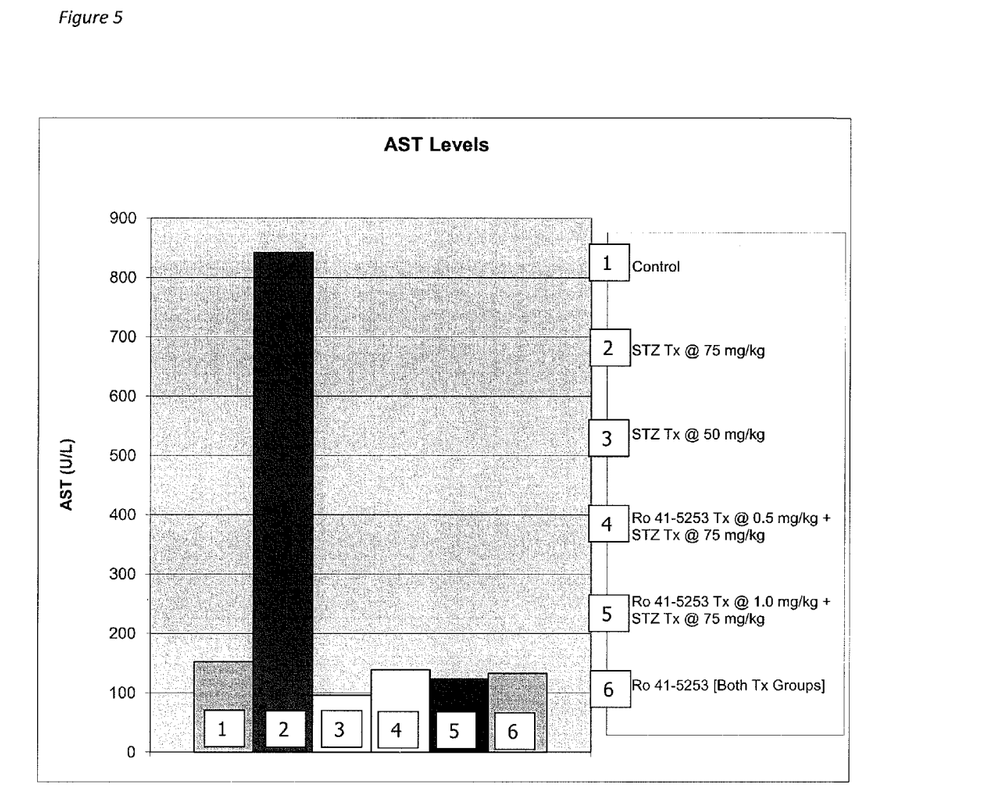
FIG. 5 is a graph showing that aspartate aminotransferase levels induced by STZ at 75 mg/kg were markedly reduced by the retinoid receptor antagonist.

The hypothesis is proposed that GDM, PREEC and FGR are initiated by an early signal from the conceptus that, in susceptible women (e.g., those with a high body mass index [BMI], preexisting diabetes, hypertension and/or liver disease), triggers a hormonal response that leads to progressive liver dysfunction; the latter in turn impairs the uptake of glucose from the circulation, causing hyperglycemia as well as impairing the production and secretion of retinol-binding protein, causing retinoids to accumulate in the liver and resulting in the low plasma retinol concentrations typically found in women with preeclampsia and infants that are small-for-gestational age. At the same time, potentially toxic retinyl esters begin to leak from damaged hepatocytes, and biliary substances that include retinoic acid and other vitamin A metabolites are refluxed from the liver into the circulation. These retinoid compounds are postulated to have a variety of toxic effects that contribute importantly to maternal and fetal morbidity and mortality and to later cardiovascular disease. On this model, liver dysfunction impairs the uptake of glucose and the mobilization and secretion of RBP and at the same time results in the spillage of toxic retinoids into the maternal and fetal circulation, causing endothelial dysfunction and preeclampsia by impairing vascular endothelial growth factor (VEGF)-associated increases in nitric oxide (NO) and vasodilatation. FGR and small-for-gestational age birth result from a direct inhibitory effect of retinoids on placentation and fetal growth. Likewise, the very low birth weight (VLBW) syndrome (including retinopathy of prematurity, bronchopulmonary dysplasia and necrotizing enterocolitis) is conjectured to result from retinoid spillage and toxicity. Later onset diabetes and vascular disease are conjectured to result from the impact of increased retinoid tissue concentrations, e.g., in the liver, that predispose to liver dysfunction and to subsequent hyperglycemia and insulin resistance; and, in the vascular beds, from retinoid-induced basement membrane and intimal wall thickening, leading to subsequent cardiovascular disease (see FIG. 1, below).

Retinoids are mainly dietary-derived, fat-soluble molecules that are stored principally in the liver (about 80%) and are essential for normal cellular homeostasis, embryonic development, tissue differentiation, growth, and mucus secretion (Theodosiou et al., 2010). The active form of vitamin A is retinoic acid (RA), which binds to and activates specific retinoic acid receptors (RARs) and retinoid X receptors (RXRs) that regulate the transcription of many target genes (Mark et al., 2006; Manicassamy and Pulandran, 2009). The RARs and RXRs are members of the steroid/thyroid superfamily of ligand dependent nuclear transcription factors that include the steroids, retinoids, thyroid hormones, and vitamin D. RA also regulates other nuclear receptors including the peroxisome proliferator-activated receptors (PPARs), the liver X receptor, and farnesoid X receptor (Huang et al, 2010). RA is produced from free retinol by hydrolysis of retinyl esters stored in the liver. Retinol is released into the circulation and delivered to the target organ tissues bound to retinol-binding protein (RBP). Retinol is first oxidized to retinaldehyde and RA is synthesized from retinaldehyde via the enzyme retinaldehyde dehydrogenase. Serum retinol levels are carefully controlled by the liver and remain stable despite major fluctuations in dietary intake, ensuring that the target tissues receive the necessary amounts of retinol.

Vitamin A Toxicity

While low concentrations of retinoic acid (RA) are essential for multiple biological functions, higher concentrations inhibit cell growth and are cytotoxic, mutagenic and teratogenic. RA is a 40-fold more potent teratogen than retinol. Vitamin A toxicity can occur as a result of excessive dietary intake or supplementation that exceeds the capacity of the liver to store the vitamin, or from treatment with synthetic retinoids. An endogenous form of retinoid intoxication can also occur naturally during cholestasis, when vitamin A metabolites are refluxed into the circulation from the liver in bile acids (Leo and Lieber, 1988). Vitamin A toxicity is generally associated with increased levels of retinyl esters circulating with plasma lipoproteins unbound to RBP. Retinyl esters react more randomly with cell membranes than the physiologically-sequestered RBP and hence are a major form of vitamin A toxicity. Fasting retinyl ester concentrations >10% of total circulating vitamin A (retinol plus esters) are considered a biomarker for toxicity (Penniston and Tanumihardjo, 2006).

Serum retinol concentrations (normally 1-3 µmol/L) vary little despite major alterations in vitamin A intake and do not reflect hepatic vitamin A concentrations over a wide range of liver values, since the secreted RBP is under homeostatic control. Case reports of hypervitaminosis A often show serum retinol concentrations within normal limits, indicating that serum retinol is not a valid measure of vitamin A status during toxicity. Studies suggest that >75% of people in developed countries routinely consume more than the recommended dietary allowance (RDA) for vitamin A. Vitamin A is considered an antioxidant vitamin and supplements are widely available as measures to prevent disease. However, a review of clinical trials on the effect of antioxidant supplements (including vitamin A) on mortality showed that the better designed ("low bias") trials were associated with a significant 7% increased risk of mortality with beta-carotene, a 16% increased risk with vitamin A, and a 4% increased risk with vitamin E, suggesting that treatment with beta-carotene and vitamins A and E may increase mortality (Bjelakovic et al., 2007).

Evidence Supporting the Retinoid Toxicity Hypothesis

The author's hypothesis is that an accumulation of retinoids occurs in the liver in early pregnancy, possibly due to hyperestrogenemia following a signal from the conceptus, leading to hepatocyte activation and inflammation, which in turn impairs the hepatic uptake of glucose as well as the mobilization and secretion of retinol from the liver into the circulation in the form of retinol-binding protein (RBP). At the same time, stored retinoids in bile and from damaged hepatocytes are spilled into the maternal and fetal circulation, contributing to the development of GDM-PREEC-FGR as a function of the toxic effects of excess circulating retinoid compounds in addition to other adverse birth outcomes, ranging from prematurity to congenital defects and stillbirth, depending on the concentration and timing of exposure to retinoids. Retinoid exposure in utero in turn is hypothesized to explain the increased risk of adult-onset diabetes and other chronic vascular diseases following preeclampsia and fetal growth restriction.

It is well known that pregnancy increases the sensitivity of the bile ducts to estrogen and that cholestasis often develops during the second and third trimesters of pregnancy (insert ref.) Cholestasis, a disturbance of bile secretion resulting from a defect in bile formation at the level of hepatocytes or from impaired bile secretion and flow at the bile duct level, is a common and severe manifestation of many liver diseases (ref). Various compounds including retinoids accumulate as a result of bile secretory failure in cholestasis and induce complex adaptive mechanisms that account for the biochemical hallmarks of cholestasis (e.g., elevated serum and urinary bile acid levels; the appearance of hydroxylated, sulphated, and glucuronidated bile acid metabolites; elevated conjugated bilirubin) as well as many clinical hallmarks in cholestasis (e.g. jaundice, bilirubinuria and pruritus). Cholestasis is the second most common cause of jaundice during pregnancy and is often associated with generalized itching (pruritus gravidarum). Cholestasis of pregnancy tends to run in families. Symptoms usually disappear within 2-4 weeks after birth but may reoccur in subsequent pregnancies (ref).

Retinoids are highly teratogenic and are known to induce growth inhibition. Perturbations in retinoids during pregnancy due to nutritional supplementation or therapy with synthetic retinoids can result in neural tube defects, other severe congenital defects, or death (ref). However, aside from consistently low serum concentrations of retinol in preeclampsia and low birth weight infants, little is known about the role of endogenous retinoids in pregnancy-related conditions and birth outcomes. Several lines of evidence support the hypothesis that an endogenous form of retinoid toxicity associated with liver dysfunction contributes to GDM-PREEC-FGR.

Liver Dysfunction in Pregnancy and FGR

Liver dysfunction comprises a spectrum of adverse conditions ranging from asymptomatic fatty liver to nonalcoholic fatty liver disease to cirrhosis. Abnormal liver tests are reported in 10% of pregnancies overall, suggesting reduced liver metabolic capacity in late pregnancy (Everson, 1999). Several conditions affecting the liver occur in pregnancy, including PREEC, HELLP syndrome (hemolysis, elevated liver enzymes, and low platelet count), acute fatty liver of pregnancy, hepatic infarction and rupture (Hunt, 1999). The association between hepatic dysfunction and PREEC has long been recognized (Barron et al., 1992; Goulis et al., 2004; Steingrub, 2004). Preeclampsia and other adverse maternal and fetal outcomes occur in a high proportion of primary disorders of the liver in pregnancy, e.g., acute fatty liver of pregnancy (Yang et al., 2000). Obstetric cholestasis is rare (<1%) but milder forms of cholestatic liver disease are more prevalent than usually believed (Martin et al., 2003). Indeed, the prevalence of fatty liver in the adult U.S. population is now over 30% and almost universal in obese persons with type 2 diabetes (Browning et al., 2004). However, up to 70% of patients with fatty liver do not show laboratory abnormalities, and liver enzymes provide only a crude indicator of fatty liver (Stefan et al., 2008). It is therefore likely that liver dysfunction in pregnancy and in preeclampsia is vastly underdiagnosed, which would support our hypothesis that asymptomatic liver dysfunction may contribute to GDM-PREEC-FGR. A study of 41 liver specimens from 41 women with PREEC with and without liver dysfunction to determine the amount of fat deposited in hepatocytes found that all 41 specimens stained with oil red O on frozen sections showed a significant amount of microvesicular fat droplets in varying degrees. In contrast, only 11 of the 41 stained conventionally with hematoxylin-eosin showed significant fatty infiltration. The density of hepatocellular fat correlated positively with plasma urate concentration and negatively with the platelet count. These findings were interpreted by the authors as suggesting that PREEC may be a microvesicular fatty disease of the liver, of which acute fatty liver of pregnancy may be the most severe manifestation (Minakami et al., 1988). The presence of liver dysfunction is increasingly evident in the progression of PREEC to more severe pregnancy-related disorders. Hepatic dysfunction in women with PREEC causes upper epigastric pain, a common feature of the disorder (Walker, 2000). Intrahepatic cholestasis of pregnancy (ICP) and other liver diseases in pregnancy are associated with poor perinatal outcomes, including fetal distress, preterm labor, and unexplained fetal death (Wolf, 1996; Mullally and Hansen 2002). Women who develop cholestasis are also at high risk for PREEC and poor fetal growth, although the mechanism is not well understood (Vega et al., 1993). An animal model of gestational diabetes induced by the antibiotic drug streptozotocin (STZ) is characterized by cholestasis and a preeclampsia-like condition as well as fetal growth restriction (Ishihara et al., 2000).

Vitamin A in Preeclampsia

Serum retinol and RBP concentrations are significantly decreased in women with PREEC and in SGA newborns compared to controls. The low retinol and RBP levels seen in PREEC and in SGA/preterm infants have been interpreted as indicating maternal-fetal undernutrition (Ziari et al., 1996; Zhang et al., 2001; Wardle et al., 2001), which is believed to be an underlying cause of the association between SGA and later-onset CVD (Barker, 2008). However, vitamin A supplementation is not associated with marked improvement in pregnancy-related conditions or birth outcomes (Shey et al., 2002) and does not alter the incidence of PREEC in multi-center clinical trials (Gilbert et al., 2008). This suggests that neither PREEC nor SGA are due to vitamin A deficiency and that the low serum vitamin A levels themselves are not due to reduced vitamin A intake but reflect a problem in vitamin A metabolism. Reduced but not deficient serum vitamin A levels may instead reflect an impairment in the hepatic mobilization of vitamin A. In fact, hepatic dysfunction impairs the synthesis and secretion of RBP, leading to reduced plasma levels of vitamin A but increased concentrations in the liver (Imamine et al., 1996). Low serum retinol levels do not provide a valid indicator of tissue levels of vitamin A or overall nutritional status. Plasma vitamin A levels (retinol), while often elevated in hypervitaminosis A, can also be normal or low (Olson, 1996; Sarles et al., 1990).

Liver Dysfunction is Associated with Hypo- and Hypervitaminosis A

It is suggested that liver dysfunction not only impairs the secretion of vitamin A, resulting in the low plasma retinol and RBP levels reported in PREEC and in SGA infants, but also results in the reflux of biliary metabolites of vitamin A and the leakage of toxic retinyl esters, unbound to RBP, into the circulation via damaged hepatocytes (Popper and Schaffner, 1985). In fact, it is known that a condition of hypo- and hypervitaminosis A can occur simultaneously (Mezey, 1982). It is therefore predicted that vitamin A metabolites will be present in high concentration in the circulation of women with preeclampsia, with adverse effects on fetal and birth outcomes. Serum bile acids are in fact markedly above normal in cholestasis, and many active metabolites of retinol, retinyl acetate, retinal, and retinoic acid are excreted in the bile (Leo and Lieber, 1986; Frolik, 1984). Bile contains retinoyl beta-glucuronide, retinoic acid, retinotaurine, and other metabolites of vitamin A, e.g., all-trans-retinoic acid, 13-cis-retinoyl beta-glucuronide, all-trans-4-oxo-retinoic acid, all-trans-18-hydroxy-retinoic acid, 9-cis-18-hydroxy-retinoic acid, and a glucuronide of beta-cis-4-ketoretinoic acid (Frolik, 1984, pp. 189-90; Olson, 1996). Polar metabolites predominate, including retinoyl beta-glucuronic acid (a metabolite of retinoic acid), all-trans-retinoic acid, and beta-cis-retinoyl glucuronides.

Retinoids can Cause FGR/SGA

Exposure to excess retinoids early in pregnancy is known to cause neural tube defects, other severe congenital anomalies or death (ref). It has been suggested that retinyl esters and metabolites of vitamin A spilled from the liver in mid-gestation enter the maternal and fetal circulation and cause GDM-PREEC-FGR, prematurity and other adverse effects, depending on the concentration and timing of exposure to retinoids during gestation. Thus the abnormal cytotrophoblast invasion of the spiral arteries and resulting impairments in placental perfusion and fetal growth may be due to an active process of growth inhibition resulting from exposure to increased concentrations of retinoid compounds in the maternal circulation. However, these forms of vitamin A have not been measured in preeclampsia nor in SGA infants. Consistent with the hypothesis, abrupt cessation of embryonic growth and growth arrest in children are well-recognized effects of RA and are characteristic of hypervitaminosis A (Moore, 1957, p. 347; Steele et al., 1983; Ganguly, 1989). Growth depression is also observed in rats fed retinoic acid (Kurtz et al., 1984). If this hypothesis is correct, physiologically high levels of retinoic acid may cause fetal growth restriction, SGA/LBW and prematurity, while early exposure to higher concentrations would be expected to cause neural tube defects, other severe congenital anomalies, or death. Retinoids, including all-trans-retinoyl-beta-glucuronide (all-trans RAG) are highly teratogenic (Shalita, 1988). In pregnant rats, subcutaneous injection of all-trans-RAG on day 8.5 of gestation is associated with a dose-dependent increase in LBW and reduced length (Ueltschy et al., 2002).

Preliminary Studies

Retinoids other than retinol and RBP have seldom been measured in GDM and have never been assessed in PREEC-FGR or SGA. As noted, the antibiotic drug streptozotocin (STZ) induces a preeclampsia-like condition and diabetes in rats (Ishihara et al., 2000) and thus provides a convenient animal model for testing purposes. What follows is data on endogenous retinoid profiles in pregnant rats after the administration of STZ, and on the effect of a retinoid receptor antagonist on this animal model.

The specific aims of the initial study were to determine whether STZ administration is associated with low or normal plasma levels of retinol, as is typically found in preeclampsia and in low birth weight infants, but also with an increased percentage of retinyl esters, an increased ratio of retinyl esters to retinol, and increased retinoic acid concentrations.

Methods

Pregnant Sprague-Dawley rats on day 6 of gestation were randomly assigned to STZ at 75 mg/kg I.P. or saline-infusion. On day 19, carotid artery catheters were implanted for measurement of arterial pressure, after which the animals were sacrificed, fetal and placental weights determined and blood samples obtained to measure liver enzymes and glucose. Subsequently, using the same procedure, a separate group of pregnant rats (n=10/group) was randomly assigned to receive STZ at 75 mg/kg I.P. or saline infusion. Serum concentrations of retinol, retinoic acid, and retinyl esters were determined in these animals by HPLC on Day 20. Retinoid toxicity was defined as the percentage of retinyl esters >10%.

Serum samples were thawed under yellow lights and extracted using a published procedure (Penniston et al., 2003). Serum (0.2-1 mL) was placed into a test tube and 2 mL of ethanol (0.1% BHT), 2 mL of ethyl acetate and 40 µL of 3,4-didehydroretinyl acetate (0.23 nmol, DRA) were added. DRA was synthesized in the laboratory using published procedures (Barua and Ghosh, 1972; Tanumihardjo et al., 1987). DRA was used as an internal standard to correct for variable recovery. After being mixed for 30 s on a vortex and centrifuged for 1 min at 1380×g, the supernatant was poured into a separate test tube. The residual pellet was washed twice with 1 mL ethyl acetate each time. The ethyl acetate layers were pooled, mixed on a vortex, centrifuged and saved for later use. A series of three extractions were performed on the supernatant. First, 2 mL of purified water and 0.5 mL hexane were added, and the mixture was mixed on a vortex and centrifuged. The top (organic) phase was removed by pipette and reserved. To the remaining aqueous phase was added 50 µL of 10% (v/v) acetic acid and the ethyl acetate from the pellet washes. After mixing on a vortex and centrifugation, the organic phase was removed by pipette and added to the first extraction. The remaining aqueous phase was extracted a third time with 1 mL hexane. The remaining aqueous material was discarded. A final wash was performed on the pooled organic material with 1 mL purified water. After mixing on a vortex and centrifuging, the organic phase was removed by pipette and placed into a clean test tube. This final material was dried under argon, reconstituted with 100 µL 80:20 methanol/dichloroethane, mixed on a vortex, sonicated to ensure complete reconstitution, and centrifuged.

A 50-75 μL aliquot was injected onto a reversed-phase gradient HPLC system consisting of a Waters 600E multisolvent delivery system and controller (Milford, Mass.) set at a flow rate of 1.0 mL/min. A Waters 2487 dual wavelength absorbance detector was set at 335 nm. A linear 20-min gradient of 70:30 methanol/water to 80:20 methanol/dichloroethane (with 10 mmol/L ammonium acetate in each solvent) was used, followed by 30 min of isocratic elution. After this the solvent was returned to baseline conditions and 10 min was allowed between injections for column equilibration. The stationary phase was a Phenomenex Phenosphere 5-μm, reversed-phase, C-18 ODS column, 150×4.6 mm (Torrance, Calif.). A Shimadzu C-R7A Chromatopac data processor (Kyoto, Japan) recorded and calculated peak areas. A precolumn was used to protect the analytical column from particulate matter. Extraction efficiency, estimated by recovery of internal standard, was 92±9.5%. The CV for this serum extraction method was calculated to be 13.2% for total vitamin A, which includes retinol, retinyl esters and metabolites.

Retention times of retinoid standards 4-oxoretinoic acid (ORA), 4-oxoretinol (OROL), retinoyl-β-D-glucuronide (RAG), atRA, 13-cis-RA, ROL (retinol), retinyl acetate, retinyl butyrate, retinyl laurate, retinyl myristate, retinyl linoleate, retinyl oleate, retinyl palmitate and retinyl stearate were used in conjunction with Photodiode Array (PDA) analysis for the identification and characterization of retinyl esters and metabolites in the rat serum. The PDA system scanned from 210 to 550 nm (Waters 600 solvent delivery system, 717 autosampler, and 996 detector) using remnant extracts from the primary analysis and 1 ml of pooled serum left-over from the primary analysis.

Results:

In the first group of rats tested, blood glucose levels were significantly elevated ($\mu$=104 mg/dL vs. $\mu$=533 mg/dL, P<0.001) and pup weights were lower than controls in the group receiving 75 mg/kg STZ ($\mu$=4.6 g vs. $\mu$=1.4 g, P<0.05). STZ at 75 mg/kg led to significantly increased alkaline phosphatase ($\mu$=123 U/L vs. $\mu$=576 U/L, P<0.001), alanine aminotransferase ($\mu$=63 U/L vs. $\mu$=326 U/L, P=0.0019), and asparate aminotransferase levels ($\mu$=152 U/L vs. $\mu$=842 U/L, P<0.05). A non-significant trend towards increased levels of arterial pressure was noted in the groups receiving both doses of STZ (P=0.1386). Thus, STZ at 75 mg/kg I.P. induced a preeclampsia-like state, altered glucose metabolism, FGR, and increased liver enzymes.

In the second group of rats, from which the retinoid values were derived (see Table 1, below), comparisons between the STZ (75 mg/kg I.P.) and control group using an exact non-parametric Mann-Whitney test revealed the following retinoid profile:

1) a significantly lower median plasma retinol (ROL) concentration in the experimental versus the control group (median, 0.45 vs. 1.04 μmol/L; p-value=0.012);
2) no significant difference for total retinol (median, 0.78 vs. 1.24 μmol/L; p-value=0.255) or total ester (median, 0.22 vs. 0.13 μmol/L; p-value=0.112);
3) a significantly higher retinyl ester/ROL ratio in the experimental group (median, 0.33 vs. 0.13; p-value=0.005);
4) a significantly higher percent ester level (median, 23.96 vs. 11.25%; p-value=0.008); and
5) a significantly higher concentration of all-trans-retinoic acid (median, 0.0155 vs. 0.0075 μmol/L; p-value=0.045).

The second study was designed to determine, based on the retinoid toxicity hypothesis and using the same animal model, whether a retinoid receptor antagonist would be effective in ameliorating the symptoms of experimental gestational diabetes. Several observations suggest that liver dysfunction and resulting alterations in retinoid (vitamin A) metabolism contribute to diabetes and its complications. Gestational diabetes mellitus (GDM) in particular is associated with reduced retinol concentrations, which could suggest impaired hepatic mobilization of vitamin A. Thus, it was hypothesized that the signs and symptoms of GDM are due in part to the spillage of stored and potentially toxic metabolites of retinol into the maternal and fetal circulation and that these symptoms can be treated using a retinoid receptor antagonist.

The specific aims of this second experiment were to test the hypothesis that complications associated with GDM could be ameliorated with the retinoic acid receptor-alpha (RAR-alpha) antagonist, Ro41-5253. On day 6 of gestation, Sprague-Dawley rats were randomly assigned to one of five groups: 1) saline-infused controls; 2) STZ, 75 mg/kg I.P.; 3) STZ, 50 mg/kg I.P.; 4) STZ, 75+Ro41-5253 (0.5 mg/kg I.P. daily for 10 d); or 5) STZ, 75+Ro41-5253 (1.0 mg/kg I.P. daily for 10 days). Ro41-5253 was provided as a gift from Roche. On day 19, after carotid artery catheters were implanted for measurement of arterial pressure, the animals were sacrificed, fetal and placental weights were determined, and blood samples were obtained to measure liver enzymes and glucose.

Results indicated (as partially described above in the first experiment) that blood glucose levels were significantly higher in the STZ 75 mg/kg group in all groups compared to saline controls ($\mu$=533 mg/dl vs. $\mu$=104 mg/dl, P<0.001). Fetuses were also smaller than controls in all groups receiving 75 mg/kg of STZ alone. Ro41-5253 had a dose-response effect on blood glucose following STZ at 75 mg/kg, with no effect of the 0.5 mg/kg dose but a decrease of approximately one-third with the 1.0 mg/kg dose. STZ at 75 mg/kg increased alkaline phosphatase levels in all animals, with or without the RAR-alpha antagonist. In contrast, elevations in alanine aminotransferase (ALT) and aspartate aminotransferase (AST) following STZ administration were markedly reduced (almost to control levels) by I.P. injection of Ro41-5253. The trend towards increased arterial pressure, seen in the groups receiving the higher dose of STZ, did not appear to be ameliorated with the RAR-alpha inhibitor at the doses investigated. Placental weights were unaffected either by STZ or the RAR-alpha antagonist (see FIGS. 2-5, below).

Discussion/Conclusions:

It was concluded that STZ at 75 mg/kg I.P. induced features of GDM (abnormal glucose metabolism), preeclampsia (increased blood pressure) and FGR (reduced pup weights). Although blood pressure was higher but not significantly so in the experimental group, it should be noted that blood pressure is normally low in healthy pregnancy, so that even in preeclamptic states blood pressure would not be expected to rise to levels greatly above those of healthy controls. Results of the retinoid assays were consistent with predictions based on the retinoid toxicity hypothesis. Plasma retinol was significantly lower in the experimental animals than in the controls. On the other hand, the percentage of retinyl esters, the ratio of retinyl esters to retinol, and retinoic acid concentrations, were all significantly higher than those of controls. Given that an accepted standard of hypervitaminosis A is percentage of retinyl esters >10%, the increased level found in this experiment (23.96% vs. 11.25% in the controls) supports the hypothesis that preeclampsia, gestational diabetes and FGR are expressions of an endogenous form of retinoid toxicity associated with impaired liver function, as indicated by increased liver enzymes. The model suggests that reducing liver and/or circulating levels of retinyl esters and retinoic acid could prevent and reverse these pregnancy-related conditions as well as FGR.

The results thus support the hypothesis that STZ induces hepatic dysfunction which in turn initiates the sequence of adverse events leading to GDM-PREEC-FGR and SGA via alterations in retinoid metabolism and exposure to toxic retinoid compounds released into the maternal and fetal circulation from the cholestatic liver. This rat model of GDM induced by STZ was accompanied by FGR and liver dysfunction, indicated by increased alkaline phosphatase (AP), alanine aminotransferase (ALT), and aspartate aminotransferase (AST) levels. Administration of the RAR-alpha antagonist Ro41-5253 reduced blood glucose at the higher dose and markedly reduced levels of liver enzymes ALT and AST but not AP.

In conclusion, the assessment of altered retinoid metabolism ("retinoid profiling")—in particular, percent retinyl esters of total vitamin A—provides a simple, easy-to-run and cost-effective diagnostic test for GDM-PREEC-FGR, and hence a valuable clinical tool in the diagnosis, prevention and treatment of these conditions and of later onset liver, metabolic and vascular diseases. The results of the second preliminary study support our claim regarding a new method for treating GDM-PREEC-FGR, using a retinoid receptor antagonist.

TABLE 1

Retinoid profiles in pregnant rats treated with streptozotocin (75 mg/kg) and controls

|  | Control (n = 10) | STZ (n = 10) | p-value |
|---|---|---|---|
| Retinol (µmol/L) | | | |
| Median | 1.04 | 0.45 | 0.0115 |
| Range | 0.38-1.37 | 0.16-0.68 | |
| Total serum Vitamin A (µmol/L) | | | |
| Median | 1.24 | 0.78 | 0.2548 |
| Range | 0.53-2.01 | 0.58-2.10 | |
| Total Ester (µmol/L) | | | |
| Median | 0.13 | 0.22 | 0.1124 |
| Range | 0.03-0.49 | 0.09-1.75 | |

TABLE 1-continued

Retinoid profiles in pregnant rats treated with streptozotocin (75 mg/kg) and controls

| Ester/ROL | | | |
|---|---|---|---|
| Median | 0.13 | 0.33 | 0.0045 |
| Range | 0.04-0.40 | 0.22-10.74 | |
| % Ester | | | |
| Median | 11.25 | 23.96 | 0.0082 |
| Range | 3.7-28.6 | 14.4-83.6 | |

|  | Control (n = 8) | STZ (n = 9) | p-value |
|---|---|---|---|
| All Trans RA (µmol/L) | | | |
| Median | 0.0075 | 0.0155 | 0.0454 |
| Range | 0.002-0.100 | 0.0079-0.1065 | |

What is claimed is:

1. A method for diagnosing the conditions of gestational diabetes, preeclampsia, or fetal growth restriction when the serum concentrations of total circulating vitamin A including retinol, retinyl esters and retinoic acid in a pregnant woman in a fasting state are as follows: (1) the concentration of retinol is equal to or less than a range of 1-3 µmol/L, (2) the percentage of retinyl esters as a fraction of the total circulating vitamin A exceeds 10%, and (3) the concentration of retinoic acid exceeds the range of about 1-2 ng/ml.

2. The method of claim 1, in which the concentration of retinol is equal to or less than about 0.70 µmol/L.

3. A method for treating any one or all of gestational diabetes by administering to a pregnant woman with one or more of the said conditions a dose of a retinoic acid receptor-alpha antagonist.

4. The method as in claim 3, in which the retinoic acid receptor-alpha antagonist is Ro41-5253.

5. The method as in claim 3, in which the effective dose is approximately 1.0 mg/kg daily for about 10 days.

6. A method for reducing alanine aminotransferase and aspartate aminotransferase in the blood by administering a dose of a retinoic acid receptor-alpha antagonist.

7. The method as in claim 6, in which the retinoic acid receptor-alpha antagonist is Ro41-5253.

8. The method as in claim 6, in which the dose is approximately 1.0 mg/kg daily for about 10 days.

* * * * *